United States Patent
Maurer et al.

(10) Patent No.: US 8,231,833 B2
(45) Date of Patent: Jul. 31, 2012

(54) DIRECT OPTICAL INTERROGATION OF AGENTS IN MICRO-FLUIDIC CHANNELS UTILIZING WHISPERING GALLERY RESONATOR APPROACH

(75) Inventors: Scott Maurer, Haymarket, VA (US); Stephanie Groves, Aldie, VA (US); Kee Koo, McLean, VA (US)

(73) Assignee: Lockheed Martin Corporation, Bethesda, MD (US)

( * ) Notice: Subject to any disclaimer, the term of this patent is extended or adjusted under 35 U.S.C. 154(b) by 162 days.

(21) Appl. No.: 12/726,041

(22) Filed: Mar. 17, 2010

(65) Prior Publication Data

US 2010/0243448 A1    Sep. 30, 2010

Related U.S. Application Data

(60) Provisional application No. 61/162,929, filed on Mar. 24, 2009.

(51) Int. Cl.
*G02B 6/02* (2006.01)
*G02B 6/26* (2006.01)

(52) U.S. Cl. ......... 422/82.11; 385/15; 385/30; 385/123; 204/450; 204/600; 435/287.2; 435/287.3; 436/96; 436/104; 436/111; 356/73.1; 356/132; 356/480

(58) Field of Classification Search .................. None
See application file for complete search history.

(56) References Cited

U.S. PATENT DOCUMENTS

| | | | |
|---|---|---|---|
| 6,490,039 B2 | 12/2002 | Maleki et al. | |
| 6,798,947 B2 * | 9/2004 | Iltchenko | 385/31 |
| 7,095,010 B2 | 8/2006 | Scherer et al. | |
| 7,177,492 B2 | 2/2007 | Strecker | |
| 7,212,701 B2 | 5/2007 | Strecker | |
| 7,257,279 B2 | 8/2007 | Guo et al. | |
| 7,259,855 B2 | 8/2007 | Fan et al. | |
| 7,266,271 B2 | 9/2007 | Strecker et al. | |
| 7,271,379 B2 | 9/2007 | Fan et al. | |
| 7,389,025 B2 | 6/2008 | Smith et al. | |
| 2002/0097401 A1 | 7/2002 | Maleki et al. | |
| 2004/0146431 A1 | 7/2004 | Scherer et al. | |

(Continued)

OTHER PUBLICATIONS

F. Vollmer and S. Arnold, "Whispering-gallery-mode biosensing: label-free detection down to single molecules", Nature Methods, vol. 5., No. 7, Jul. 2008, pp. 591-596.

(Continued)

*Primary Examiner* — In Suk Bullock
*Assistant Examiner* — Timothy G Kingan
(74) *Attorney, Agent, or Firm* — Howard IP Law Group, P.C.

(57) ABSTRACT

A whispering gallery mode resonator based optical sensor assembly comprises a flow channel permeable to optical energy and first and second optical waveguides adjacent to a section of the flow channel and adapted to be in first and second evanescent field couplings respectively with the section such that the section forms a whispering gallery mode resonator. The resonator is responsive to an optical signal conveyed in the first optical waveguide and communicates a second optical signal to the second optical waveguide indicative of a resonance wavelength of the whispering gallery mode resonator. A detector optically coupled to the second optical waveguide detects the output signal. A signal processor detects a shift in the output signal responsive to an analyte fluid flowing through the flow channel. The shift is indicative of the identity of at least one constituent of the analyte fluid.

18 Claims, 12 Drawing Sheets

U.S. PATENT DOCUMENTS

| | | | |
|---|---|---|---|
| 2004/0227089 A1* | 11/2004 | Kolodzey et al. | 250/341.8 |
| 2006/0062508 A1* | 3/2006 | Guo et al. | 385/12 |
| 2007/0237460 A1* | 10/2007 | Fan et al. | 385/39 |
| 2007/0269901 A1 | 11/2007 | Armani et al. | |
| 2008/0129997 A1 | 6/2008 | Yi et al. | |
| 2008/0204709 A1* | 8/2008 | Kiesel et al. | 356/36 |

OTHER PUBLICATIONS

Laine et al., "Planar integrated wavelength-drop device based on pedestal antiresonant reflecting waveguides and high-Q silica microspheres", Optics Letters, vol. 25, No. 22, Nov. 15, 2000, pp. 1636-1638.

White et al., "Integrated multiplexed biosensors based on liquid core optical ring resonators and antiresonant reflecting optical waveguides", Applied Physics Letters 89, 191106 (2006) pp. 191106-1 to 191106-3.

* cited by examiner

DIRECT OPTICAL INTERROGATION OF AGENTS IN MICRO-FLUIDIC CHANNELS UTILIZING WHISPERING GALLERY RESONATOR APPROACH

CROSS-REFERENCE TO RELATED APPLICATION

The present application claims the benefit of the U.S. Provisional Patent Application Ser. No. 61/162,929, filed on Mar. 24, 2009, which application is incorporated by reference herein in its entirety.

FIELD OF INVENTION

The present invention relates to optical sensing devices and methods using optical resonators.

BACKGROUND

Rapid and real-time detection of chemical, biological and explosive agents without the need for elaborate laboratory facilities is desirable for many applications, including, for example, medical and security applications. Optical sensing technologies have been used for detecting agents in various fluids. Optical sensing technologies generally use an optical probe beam to interact with a material to be detected. Some aspect of the optical probe beam is modified by this interaction between the optical probe and the material. A portion of this modified beam, such as the scattered light, the reflected light, or the transmitted light, may be collected and measured to obtain certain information of the material. Under proper conditions, optical sensing is a non-invasive technique that does not materially alter the contents under measurement/test. The spectrum of a probe beam may be controlled to selectively interact with specified particles, molecules, or atoms in the material to elicit some measurable modifications in the optical beam, wherein the modifications are indicative of the identity of the material constituents. Optical sensing may also be used for applications requiring high sensitivity and/or detection of minute amounts of a particular material.

Certain known optical sensors, such as single molecule sensors, typically require a fluorescent or metallic label attached to the target molecule so that the target molecule may be identified. Such labels, however, require prior knowledge of the presence of the target molecule(s). Thus, current sensing systems that require labels are not suitable for blind detection of target molecules, which do not have labels. Labels can structurally and/or functionally interfere with an assay, or may not be specific or be difficult to conjugate. Such problems are often encountered in single molecule experiments. Furthermore, such labels may require additional data processing. For example, sensors using labels may require ensemble averaging of large numbers of cells, resulting in confusion or dulling of recorded responses in those cases in which there is heterogeneity in the cells or their responses. Current methods of detection using labels cannot be performed in real-time.

Several devices have been used for label-free detection. Such devices include fiber optic waveguides, nanowires, nanoparticle probes, biochips, mechanical cantilevers, micro-sphere resonators, and Quartz Crystal Modulator (QCM) oscillators, as well as acousto/optical and acoustic wave devices. While certain known devices may provide label-free detection, such devices have significant drawbacks. For example, various known sensors lack sufficient sensitivity to enable detection of a very small number of molecules or a single molecule, and therefore, prove unsuitable for biological and chemical analyses requiring more specific detection, such as cell signaling and cellular dynamics. Previous experiments with silica micro-spheres, for example, demonstrated gross detection of approximately 1 billion molecules. Such devices are not suitable for detection of a very small number of molecules or a single molecule.

Sensitivities of sensors having mechanical components may be limited by the sensitivities that can be achieved given the particular mechanical construct. Furthermore, such devices are often subject to electromagnetic interference. In the case of certain optical sensors and traps, sensitivity limitations are due, in part, to the limited interaction of light with the target molecule. For example, in a simple optical waveguide sensor, the input light has only one opportunity to interact with the target molecule. Accordingly, blind, real-time, and label-free molecule detection methods and sensor systems having enhanced specificity and sensitivity for detecting very small numbers of molecules or for single molecule detection are desirable.

SUMMARY OF THE INVENTION

A whispering gallery mode resonator based optical sensor assembly comprises a flow channel permeable to optical energy and first and second optical waveguides adjacent to a first section of the flow channel and adapted to be in first and second evanescent field couplings respectively with the first section such that the first section of the flow channel forms a whispering gallery mode resonator. The resonator is responsive to a first optical signal conveyed in the first optical waveguide and communicates a second optical signal to the second optical waveguide indicative of a resonance wavelength of the whispering gallery mode resonator. A first detector optically coupled to the second optical waveguide detects the output signal. A signal processor detects a shift in the output signal responsive to an analyte fluid flowing through the first section of the flow channel. The shift is indicative of the identity of at least one constituent of the analyte fluid.

According to an embodiment of the invention, a whispering gallery mode based optical sensor system includes at least one flow channel permeable to optical energy. The system further includes first and second optical waveguides adjacent to a first section of the at least one flow channel and adapted to be in first and second evanescent field couplings respectively with the first section. A light source is in optical communication with the first optical waveguide. The first section forms a first whispering gallery mode resonator responsive to a first optical signal conveyed in the first optical waveguide from the light source and communicates a second optical signal to the second optical waveguide indicative of a resonance wavelength of the whispering gallery mode resonator. An optical detector is optically coupled to the second optical waveguide for detecting the second optical signal. A digital signal processor is in communication with the optical detector for detecting a shift in the output signal responsive to an analyte fluid flowing through the first section. The shift is indicative of the identity of at least one constituent of the analyte fluid.

A method for optical interrogation of an analyte fluid comprises conveying a first optical signal via a first optical waveguide evanescent field coupled to a section of a flow channel. The section defines a whispering gallery mode resonator. The first section of the flow channel is evanescent field coupled to a second adjacent optical waveguide to provide a second optical signal in the second optical waveguide, wherein the second optical signal is indicative of the whispering gallery resonance mode of the first section. The method further includes detecting the second optical signal to identify a reference resonance wavelength, flowing an analyte fluid through the flow channel, and detecting an optical signal output from the second waveguide to identify a shift in the resonance wavelength of the output relative to the reference resonance wavelength and indicative of the identity of at least one constituent of the analyte fluid.

According to an aspect of the present invention, a whispering gallery mode resonator based optical sensor assembly is disclosed. The sensor assembly has a flow channel having a wall permeable to optical energy. At least one section of the channel forms a whispering gallery mode resonator responsive to an optical signal. First and second optical waveguides are adapted to be in first and second evanescent field couplings respectively with at least one section of the flow channel. Responsive to an input optical signal carried by the first optical waveguide, a whispering gallery mode resonance is introduced in at least one section of the flow channel via the first evanescent field coupling. The second optical waveguide receives an output optical signal from at least one section of the flow channel via the second evanescent field coupling. The output optical signal is indicative of a resonance wavelength of the whispering gallery mode resonator. Responsive to an analyte fluid flowing through the flow channel, a shift occurs in the resonance wavelength of the whispering gallery mode resonator. The shift is indicative of the identity of at least one constituent of the analyte fluid flowing through the flow channel.

According to another embodiment, a system includes a flow-channel having multiple sections, each section having a different diameter. In an exemplary embodiment, the diameter of the flow channel increases along the direction of the flow of the analyte fluid. Each section has a set of first and second optical waveguides in evanescent field coupling therewith.

BRIEF DESCRIPTION OF THE DRAWINGS

Understanding of the present invention will be facilitated by consideration of the following detailed description of the exemplary embodiments of the present invention taken in conjunction with the accompanying drawings, in which like numerals refer to like parts and in which.

DETAILED DESCRIPTION

It is to be understood that the figures and descriptions of the present invention have been simplified to illustrate elements that are relevant for a clear understanding of the present invention, while eliminating, for purposes of clarity, other elements found in typical analyte fluid analyzing sensor systems and methods and whispering gallery mode resonators. However, because such elements are well known in the art, and because they do not facilitate a better understanding of the present invention, a discussion of such elements is not provided herein. The disclosure herein is directed to all such variations and modifications known to those skilled in the art.

Figure 10A:
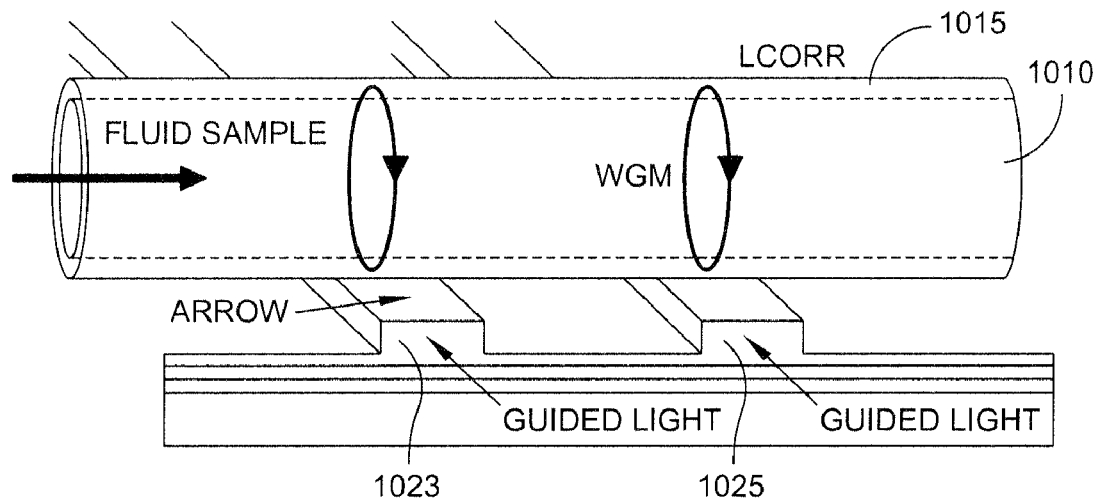
FIGS. 10A-10B are schematic front view and side view diagrams showing a prior art structure of a planar waveguide and its positioning relative to the fluidic channel to be interrogated via evanescent wave from the waveguide.
Figure 10B:
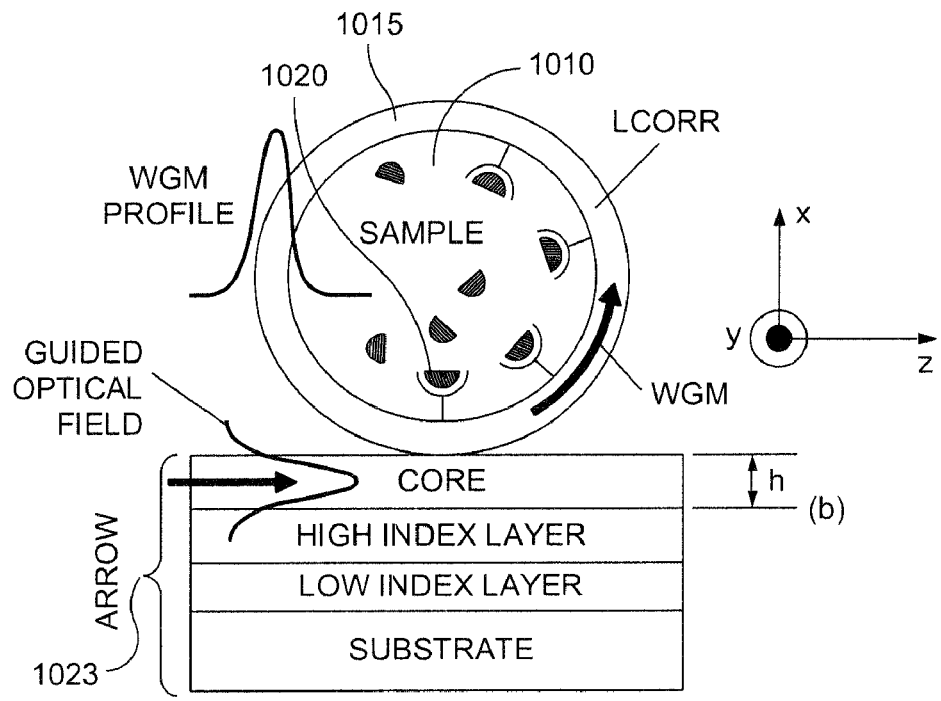

Referring to FIG. 10A-10B, there is illustrated a prior art configuration for optical interrogation of a fluid channel using an Anti-Resonant Reflecting Optical Waveguide (ARROW). A fluid sample containing analytes or particles 1020 passes through a flow channel 1010. Analyte particles 1020 are immobilized to the inner surface of flow channel 1010 by, for example, first activating the inner surface of channel 1010 before passing the sample containing analyte particles 1020. As is known in the art, inner surface 1010 may be activated by passing an adsorbent through flow channel 1010, thereby creating binding sites on inner surface for analyte particles 1020. Flow channel 1010 is optically coupled to two waveguides 1023, 1025 having a structure as depicted in FIG. 10B. Flow channel 1010 is adapted to form Liquid Core Optical Ring Resonators (LCORR) 1015, when coupled to the corresponding optical waveguides 1023, 1025 as shown in FIG. 10A.

Figure 1:
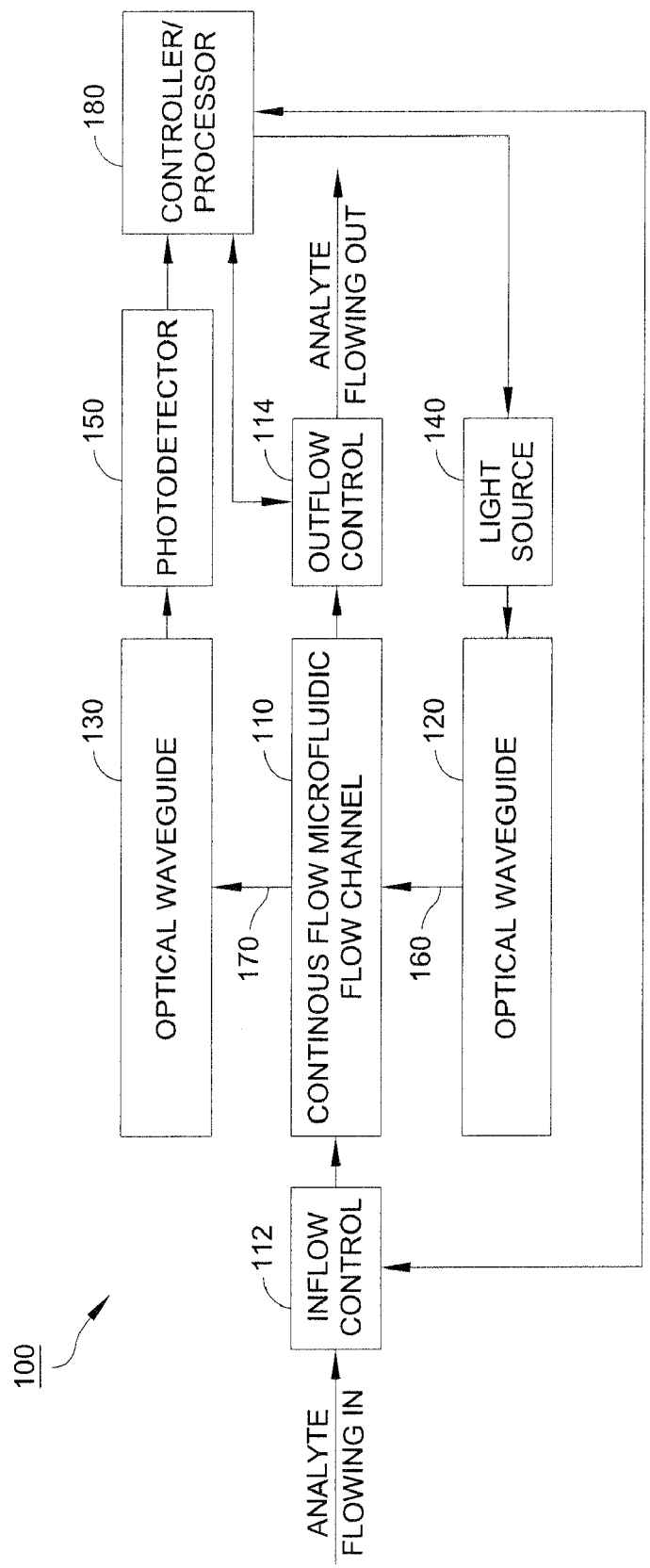
FIG. 1 is a block diagram illustrating a system for optical interrogation of an analyte fluid flowing through a flow channel coupled with two optical waveguides, according to an embodiment of the invention.

Referring now to FIG. 1, there is illustrated an exemplary block diagram of major components of a sensor assembly 100 for optical interrogation of an analyte fluid flowing through a flow channel. Sensor assembly 100 includes a flow channel 110 adapted to receive an injected analyte fluid, first and second optical waveguides 120, 130, a light source 140, a photodetector 150 and a controller/processor 180. Optical waveguide 120 and flow channel 110 are coupled via an evanescent field 160. Likewise, optical waveguide 130 and flow channel 110 are coupled via an evanescent field 170. In an exemplary configuration, controller 180 may take the form of a general or a special purpose computer and may include an integrated computerized digital signal processor and a data acquisition card (not shown) coupled to photodetector 150. Controller 180 serves to control light source 120, flow of the analyte fluid through flow channel 110, and photodetector 150. In an exemplary embodiment, the flow of the analyte fluid through flow channel 110 may be controlled by an inflow control mechanism 112 and/or an outflow control mechanism 114. The flow control mechanisms 112, 114 may, in turn, be controlled by controller 180. By way of example only, flow control mechanisms 112, 114 may take the form of a microfluidic pump, a microfluidic valve, or other known flow control mechanisms. In the illustrated embodiment, controller 180 may receive analyte fluid information (such as flow rate data) pertaining to the analyte fluid flowing into channel 110 and/or flowing out of channel 110, for example, via flow control mechanisms 112, 114. Controller 180 may also control the flow or flow rate of the analyte fluid into channel 110 and/or out of channel 110 via flow control mechanisms 112, 114. In other embodiments, controller 180 may not control the flow mechanisms 112, 114, but only receive the analyte fluid flow data pertaining to analyte fluid flowing into channel 110 and/or flowing out of channel 110. A data acquisition card may include a plug-in data acquisition card which may be plugged directly into the chassis of a computer and may include one or more analog inputs and outputs, and one or more digital inputs and outputs. Examples of suitable hardware data acquisition systems include those produced by industry vendors such as National Instruments, AD Instruments, and Fluke, etc which may be controlled with the respective vendor's data acquisition software suites such as LabVIEW, LabChart, and NetDAQ. Integration of the data acquisition controller (e.g. NI CompactRIO) with a higher level system processor in a small form factor is well known and may include small embedded, real-time controllers, and field-programmable gate arrays (FPGAs) for system control as well. Since such controllers, digital signal processors and data acquisition cards and systems are known in the art, controller 180 is not described in further detail for the sake of brevity.

Figure 2:
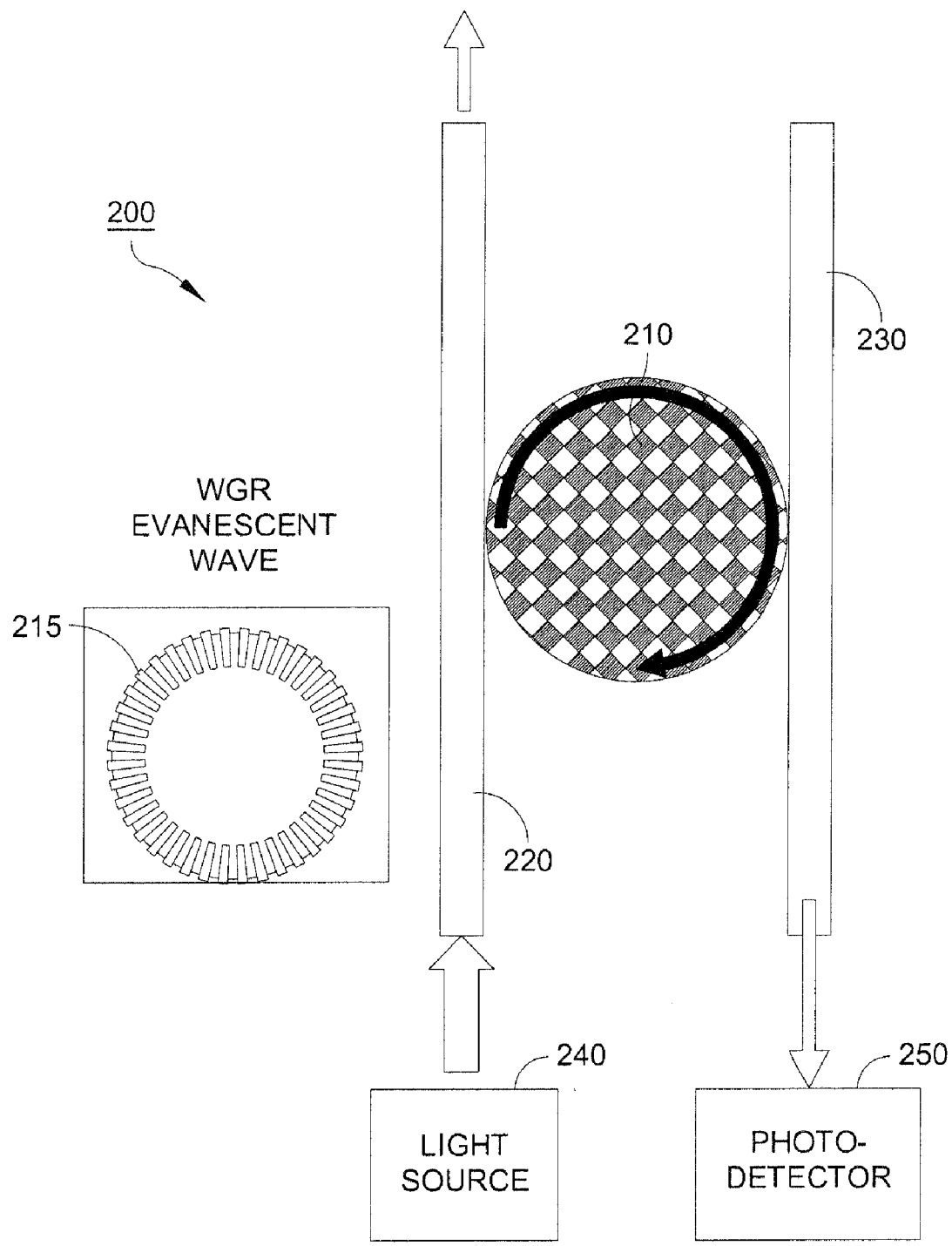
FIG. 2 is a cross-sectional view of the system of FIG. 1, according to an embodiment of the invention.
Figure 3:
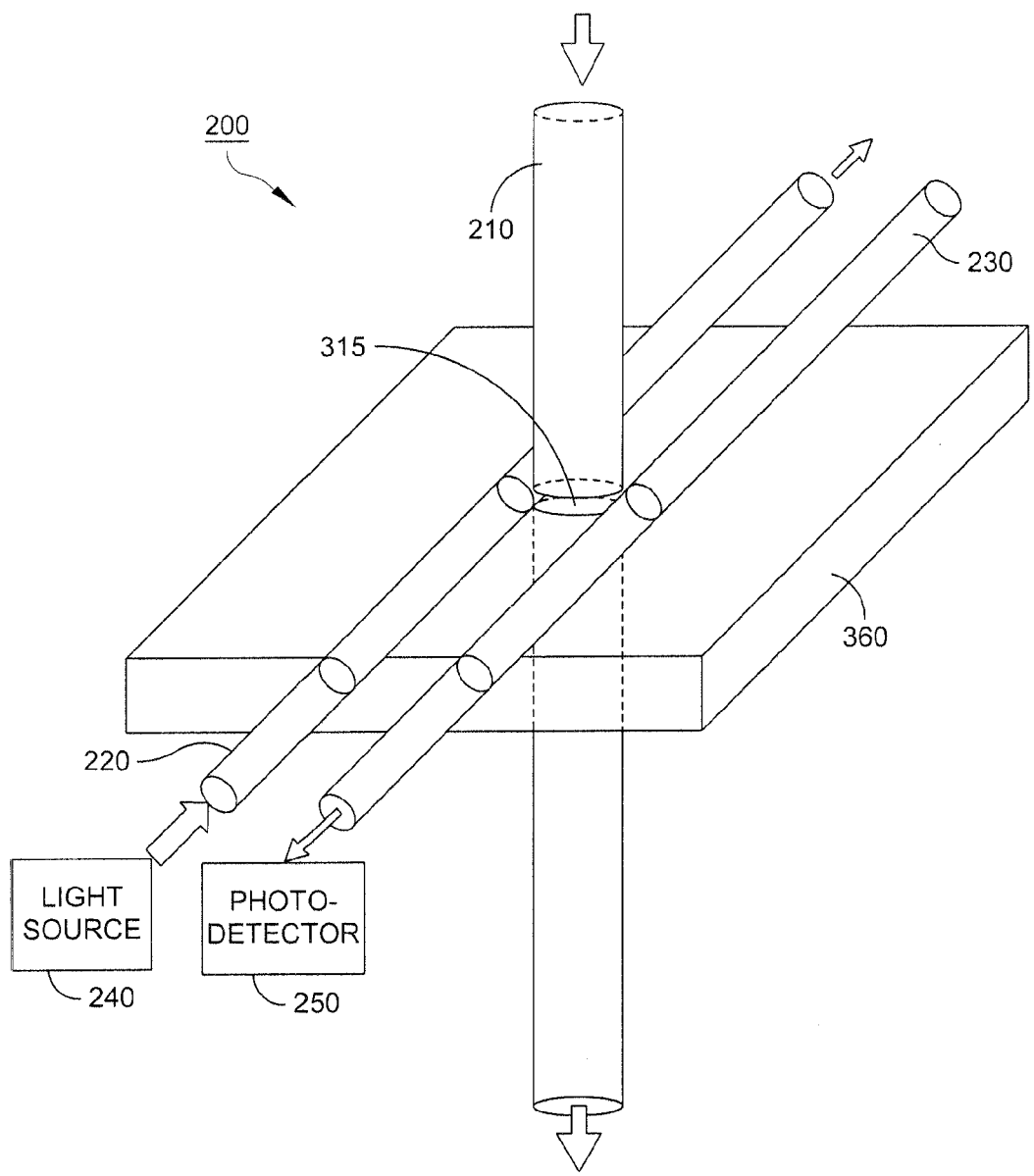
FIG. 3 is a schematic diagram of a system for direct optical interrogation of a fluid flowing through a flow channel, according to an embodiment of the invention.

Referring now to FIGS. 2 and 3, there is shown a schematic illustration of a sensor assembly 200 for direct optical interrogation of an analyte fluid flowing through a flow channel. Sensor assembly 200 includes a flow channel 210, first and second optical waveguides 220, 230 in an evanescent field coupling with flow channel 210. A light source 240 is in optical communication with waveguide 220. In an exemplary embodiment, light source 240 is a wavelength tunable light source such as a laser. In other configurations, light source 240 may be one or more Light Emitting Diodes (LEDs), a wavelength-tunable laser or a broadband light source through a tunable optical filter. A tunable light source may be used to map out analyte specific resonance wavelength signatures across a spectrum of input wavelengths. Alternatively, a broadband source may be used and the received light may be optically analyzed before the photoelectric conversion via a single detector or a detector array such as a CCD array. A detector 250 such as a photo detector is in optical communication with waveguide 230. In one configuration, detector 250 is a single detector when a wavelength-tunable input optical source is used. Alternatively, in other configurations, when a broadband light source is used as an input, detector 250 may include a stationary spectrally dispersive elements such as an optical prism or an optical axis grating or a detector array such as a CCD array or a scanning spectrally dispersive element.

In one configuration, flow channel 210 takes the form of a capillary tube. In another configuration, flow channel 210 is a continuous flow microfluidic analyte delivery channel. Continuous flow in flow channel 210 enables real-time monitoring and detection of an analyte fluid flowing through flow channel 210. Flow channel 210 may, for example, have a diameter in the range of 50 micrometers (μm) to 200 μm, a wall thickness preferably less than 5 μm and a length of about 0.1 millimeters (mm) or longer as needed. In an exemplary embodiment, flow channel 210 may be made of glass, quartz or plastics such as polystyrene (PS), polycarbonate (PC), poly (methyl methacrylate) or PMMA, polytetrafluoroethylene (PTFE)-based or polytetrafluoroethene (PTFE)-based plastics and other optically transparent thermoset plastics such as cyclo-olefin polymers sold under the trade mark Zeonor. Other transparent materials which allow optical energy to enter and exit through the walls of flow channel 210 without any significant absorption of the optical energy may also be used according to the specific requirements of a particular application. The material of flow channel 210 may be selected to have ultra-low optical loss at the frequencies of the supported whispering gallery modes. The surface of flow channel 210 may be fabricated to minimize the size of any surface inhomogeneities, e.g., on the order of a few Angstroms or to a fraction of the optical wavelength used for the interrogation, by processes such as fire polishing. One adopted fabrication process is to apply fiber drawing technique to transform appropriate macro-size capillary tubes to micro capillary tubes of the right size with good surface quality.

As shown in FIG. 3, the analyte fluid enters channel 210 at one end, flows through a section 315 of channel 210 and exits at the other end of channel 210. Section 315 is evanescently coupled to the first and second optical waveguides 220, 230. Section 315 of flow channel 210 acts as a whispering gallery mode resonator (WGMR) having a high Q-factor, and responsive to the optical signal conveyed by the first optical waveguide 220. The whispering gallery mode resonator provides an output optical signal via evanescent field coupling to the second optical waveguide 230. Second optical waveguide 230 further conveys the output optical signal to downstream photodetector 250. A "whispering gallery mode" is a special set of resonator modes which are essentially electromagnetic field modes confined in an interior region close to the surface of a structure having a generally circular cross-section and circulating by total internal reflection inside the axially symmetrical structure.

As is known in the art, Q-factor of a resonant cavity is given by:

$$Q = \frac{2\pi f_o \varepsilon}{P}$$

Where,
$f_o$ is the resonant frequency,
$\varepsilon$ is the stored energy in the cavity, and
$P=-(dE/dt)$ is the power dissipated.
Thus, the lower the power dissipated in the cavity, the higher the Q-factor of the resonator cavity. The Q-value of a circular ring resonator depends largely on the intrinsic optical loss of the resonator material and the surface optical scattering loss associated with surface roughness. A lower limit is set by the Rayleigh loss:

$$Q < 2\pi n/\lambda\alpha,$$

where $\lambda$ is the optical wavelength of interest, n is the refractive index and $\alpha$ is the Rayleigh scattering coefficient in (cm$^{-1}$). A high Q-value produces a high spectral resolution and a long interaction length between the probe light and the analyte resulting in high sensitivity. The effective interaction length ($L_{eff}$) is related to Q-value by $$L_{eff} = Q\lambda/2\pi n$$

and the resonant wavelength is related to the effective refractive index ($n_{eff}$) through the resonant condition $$\lambda = 2\pi r n_{eff}/m,$$

where r is the radius of the ring resonator and m is an integer relating to the excited whispering gallery mode.

Section 315 of flow channel 210 has a high Q-factor, greater than 10$^6$. In one configuration, section 315 of flow channel 210 may have a Q-factor of about 5×10$^7$. The high Q-factor results in higher sensitivity of sensor assembly 200. As described above, the high Q-factor of section 315 of flow channel 210 may be achieved by selecting appropriate materials and fabricating processes. The flow dynamics such as laminar flow versus turbulent flow affects the amount of mixing of the various particles of different size/mass inside the flow tube. The high Q-factor enables the detection of smaller shifts in the resonance wavelength, which shifts are indicative of the properties of the analyte fluid flowing through flow channel 210.

Section 315 as depicted in the drawings is for illustrative purposes only. In an exemplary embodiment, flow channel 210 is adapted to act as a whispering gallery mode resonator (WGMR) wherever optical waveguides 220, 230 are in an evanescent field coupling with flow channel 110. In another embodiment, one or more specific segments of flow channel 210 may be adapted to act as a whispering gallery mode resonator responsive to an optical signal. The resonant frequencies of section 315 change or shift depending on the properties of the constituents of the analyte fluid flowing through flow channel 210. Thus, the shift in the resonance frequencies is indicative of one or more constituents of the analyte fluid flowing through flow channel 210. The identity of one or more constituents may be inferred from the magnitude of the shift in the resonance wavelength. A database or library of constituents and their associated shifts in the resonance wavelength may be used by controller 180 to identify a constituent based on the shift in the resonance detected by controller 180. Initially one or more analyte fluids containing a known constituent may be flowed through flow channel 210 and the shift in resonance wavelength associated with the known constituent may be recorded to develop a database or library of known constituents and their associated shifts in the resonance wavelength. The database so developed may be then be used to identify a constituent based on the shift in the resonance wavelength detected by controller 180.

Figure 11:
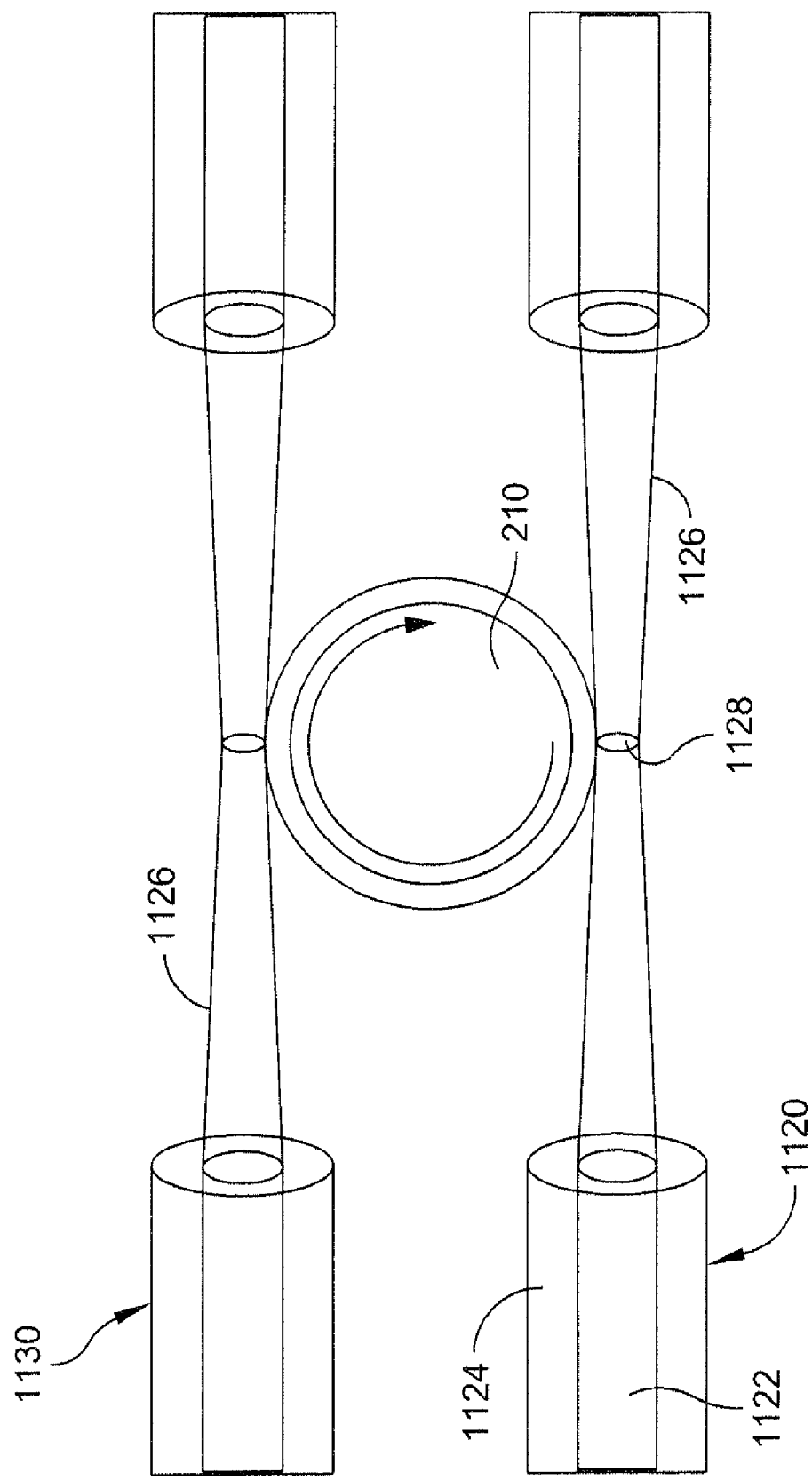
FIG. 11 is a cross-sectional view showing another embodiment using tapered optical fiber waveguides and associated positioning relative to the fluidic channel to be interrogated via evanescent waves from the optical waveguides.

Still referring to FIGS. 2 and 3, first and second optical waveguides 120, 130 are in evanescent wave or field coupling with flow channel 110. First and second optical waveguides 120, 130 are positioned on a planar platform 360. A planar platform facilitates fabrication in volume production using integrated circuit (IC) technology and integration into a sensor platform such as described in J. P. Laine, et al., "Planar integrated wavelength-drop device based on pedestal antiresonant reflecting waveguides and high-Q silica microspheres," *Opt. Lett.*, 25, 1636-1638, 2000. In one configuration, first and second waveguides 120, 130 may take the form of optical fibers. By way of non-limiting example only, first and second waveguides 120, 130 may be single-mode optical fibers. In one configuration, wave guides 120, 130 may include tapered optical fibers as illustrated in FIG. 11. FIG. 11 illustrates an embodiment having first and second optical waveguides 1120, 1130, each having a fiber core 1122 and fiber cladding 1124. A section 1126 of each fiber core 1122 has a tapered profile as depicted in FIG. 11. The tapered profile has a diameter equal to the diameter of core 1122 at one end which decreases to its minimum diameter at a section 1128. First and second waveguides 1120, 1130 are adapted to be in an evanescent wave coupling with flow channel 210 at section 1128. A tapered optical fiber waveguide allows an evanescent wave to extend further out from the fiber core providing more efficient coupling to the fluidic channel 210. Also, a specific planar waveguide structure such as the anti-resonant reflecting optical waveguide (ARROW) structure can provide evanescent wave extending further out from the waveguide core.

First and second optical waveguides 120, 130 are positioned sufficiently close to the wall of flow channel 110 to enable evanescent field coupling between flow channel 110 and first and second optical waveguides 120, 130. As an input optical signal or a light signal passes through first optical waveguide 120, an evanescent wave protrudes from the surface of optical waveguide 120 into the surrounding medium. The surrounding medium is normally air; otherwise the index of the surrounding medium needs to be included into the calculation of the coupling loss. The evanescent wave decays with a length that is related to the ratio of the index of refraction of the wall of optical waveguide 120 and the surrounding medium, and is typically on the order of 0.5 µm, for example. The thickness of the wall of optical waveguide 120 and flow channel 110 should be less than one wavelength of light so that evanescent coupling of optical waveguide 120 with flow channel 110 is possible. In an exemplary embodiment, the distance between first optical waveguide 120 and flow channel 110 may be in the range of about 20 nanometers (nm) to about 100 nm. As is known in the art, an evanescent field decays exponentially with the distance from the source of the field and is most intense within one-third wavelength from a source. Accordingly, the distance between optical waveguides 120, 130 and flow channel 110 is a function of the wavelength of a light passing through optical waveguides 120, 130.

Once an input optical signal from waveguide 220 is introduced into section 315 via the evanescent field coupling, the whispering gallery modes circulate in section 315 and produce an evanescent wave or field 215 that protrudes from the walls of flow channel 210 into the surrounding medium. Optical waveguide 230 is coupled to the evanescent field 215 from flow channel 210 and receives an output optical signal from flow channel 210. The output optical signal is indicative of the resonance wavelength of the whispering gallery mode resonator formed by section 315 of flow channel 210. The output optical signal received by waveguide 230 is detected by photodetector 250. The output of photodetector 250 is processed by processor 180 to identify one or more constituents of the analyte fluid flowing through flow channel 210 based on the shift in the resonance wavelength.

Figure 4:
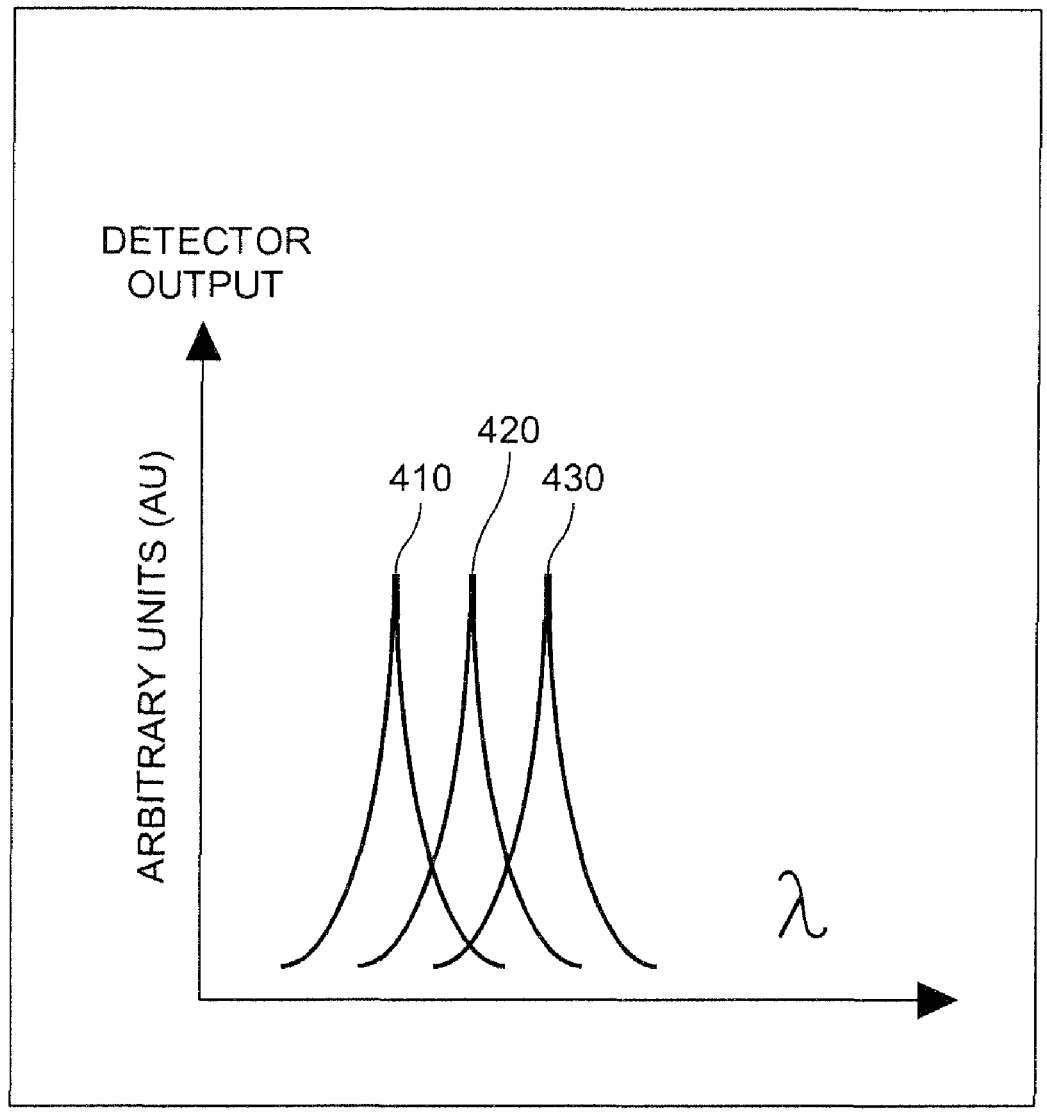
FIG. 4 illustrates resonance shifts associated with two exemplary constituents of the analyte fluid compared with a reference, as detected by a photodetector according to an embodiment of the invention.

Referring now to FIG. 4, there is illustrated a graph showing the shift in resonance wavelength resulting from two different analytes flowing through flow channel 210. The X-axis of FIG. 4 represents wavelength ($\lambda$), whereas the Y-axis represents Arbitrary Units (AU), as is customary in the art. Curve 410 represents the resonance at a specific wavelength when no analyte is flowing through flow channel 210. Curve 420 represents a shift in the resonance when Analyte 1 is flowing through flow channel 210. One or more constituents of Analyte 1 may be inferred from the magnitude of the shift in the resonance. In a similar fashion, curve 430 represents a shift in the resonance when Analyte 2 is flowing through channel 210. In a similar fashion, one or more constituents of Analyte 2 may be inferred from the magnitude of the shift in the resonance.

Figure 5:
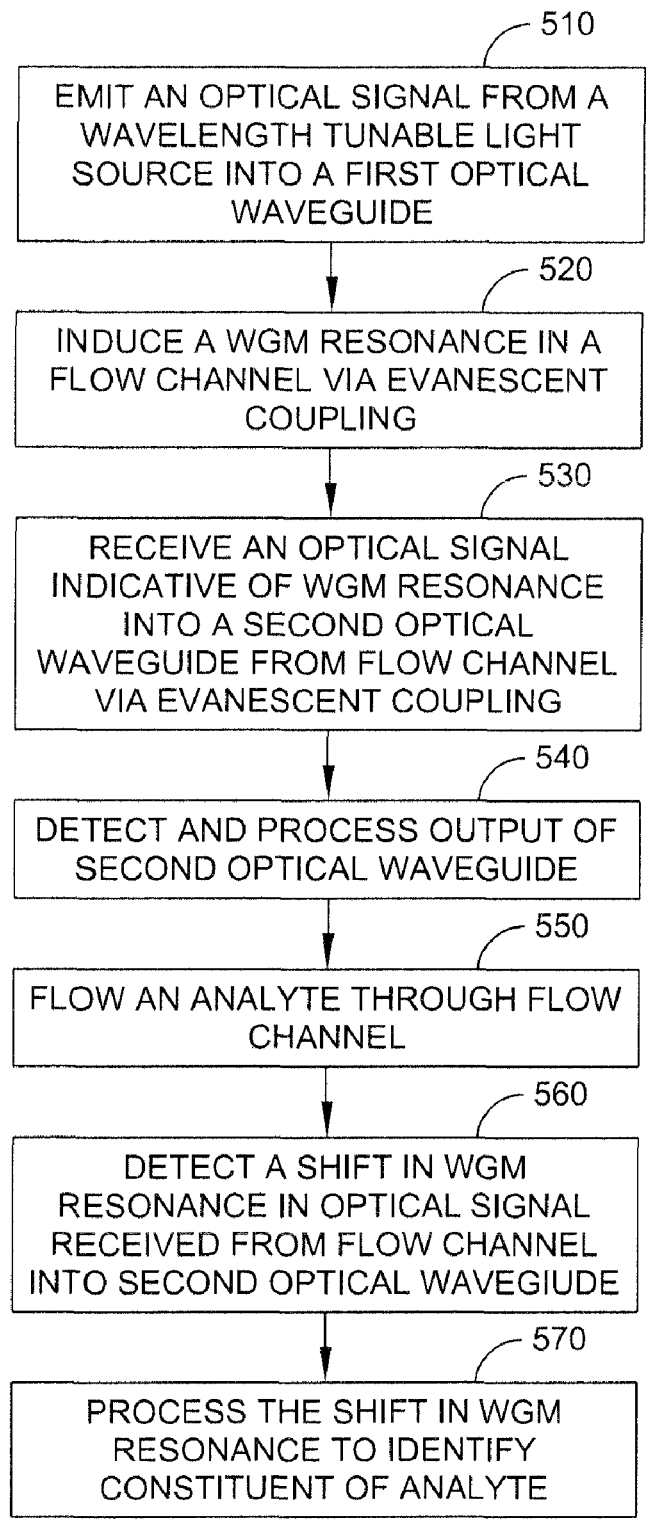
FIG. 5 is a process diagram for identifying constituents of an analyte fluid flowing through a flow channel of FIG. 1, according to an aspect of the invention.

Now referring to FIG. 5 in conjunction with FIG. 1, there is illustrated a process flow diagram for direct optical interrogation of an analyte fluid flowing through a flow channel, according to an aspect of the invention. At block 510, an input optical signal is emitted from a wavelength tunable light source 140 into a first optical waveguide 120. At block 520, a whispering gallery mode resonance is introduced in flow channel 110 via evanescent field coupling with optical waveguide 120, responsive to the input optical signal in optical waveguide 120. At block 530, second optical waveguide 130 receives an output optical signal indicative of the whispering gallery mode resonance in flow channel 110 via evanescent field coupling. At block 540, the output of second optical waveguide 130 is detected by photodetector 150 and processed by processor 180 to identify the specific wavelength of light at which resonance is identified. The identified wavelength serves as a reference wavelength. At block 550, an analyte fluid is flowed through flow channel 110. At block 560, a shift in the resonance in flow channel 110 resulting from the presence of the analyte is detected via second optical waveguide 130 and photodetector 150. At block 570, the shift in resonance is processed and analyzed to infer the constituents of the analyte fluid flowing through flow channel 110 based on a library or database of constituents and their associated shifts in the resonance wavelengths, as described earlier.

In yet another embodiment, assembly 200 shown in FIG. 2 may be adapted such that flow channel 210 includes first and second capillary tubes. Each of the two capillary tubes is configured as shown in FIG. 2 with adjacent first and second optical waveguides, input optical source signal coupled to the first waveguide, and optical detector coupled to the output of the second optical waveguide. In this configuration, a base or a control sample may be injected or filtered through the first capillary tube. An analyte fluid may be injected or filtered through the second capillary tube. A first whispering gallery mode resonance shift in the first capillary tube indicative of the base or control sample is induced and detected by the associated first and second optical waveguides respectively. Likewise, a second whispering gallery mode resonance shift in the second capillary tube indicative of the analyte is induced and detected by the associated first and second optical waveguides respectively. The first and the second whispering gallery mode resonance shifts may then be analyzed differentially or ratiometrically to identify one or more constituents of the analyte fluid flowing through the second capillary tube.

Figure 6:
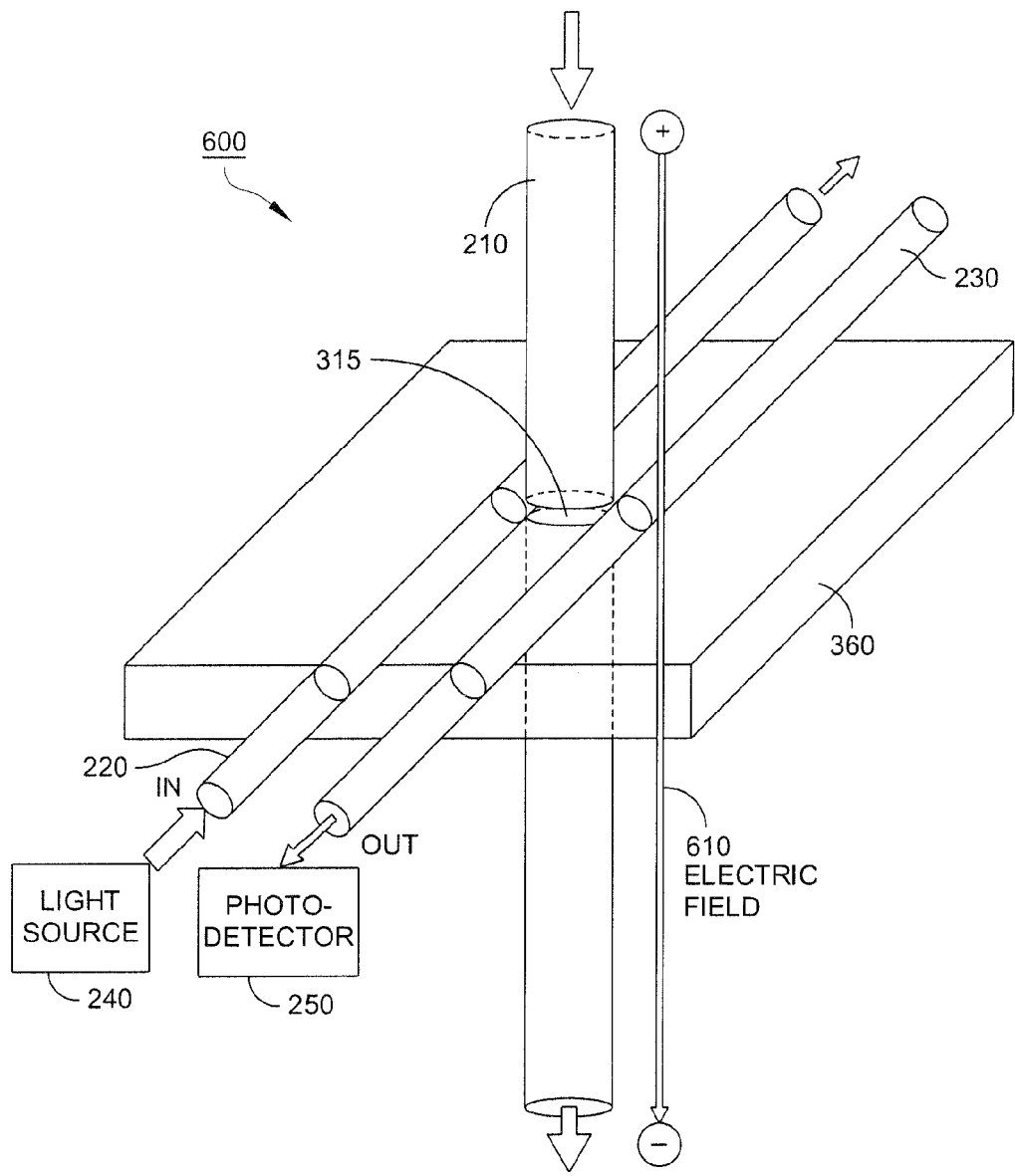
FIG. 6 illustrates a schematic diagram of a system, with electrophoretic control, for direct optical interrogation of a fluid injected into the flow channel, according to another embodiment of the invention.

FIG. 6 illustrates another embodiment of the invention. Sensor assembly 600 is generally similar to sensor assembly 200 shown in FIG. 2. An electric field 610 is applied to flow channel 210 and therefore to the analyte fluid flowing through flow channel 210. As is known in the art, electrophoresis is the motion of dispersed particles in a fluid relative to the fluid under the influence of an electric field that is space uniform. Electrophoresis is used to control the flow dynamics of the analyte fluid injected into flow channel 210. In an exemplary embodiment, the flow channel 210 is filled with a gel such as acrylamide or polyacrylamide that is used to contain and then separate the target molecules. The polarity of electric field 610 depends on the charge distribution of the target molecules to be separated. The molecules move through the gel matrix at different rates, determined by their sizes/masses, towards the anode if negatively charged or toward the cathode if positively charged. Therefore, if the target molecules to be separated and detected are DNA samples, for example, which are negatively charged, then an electric field may be applied with negative polarity at the top of the channel and positive polarity at the bottom of flow channel 210.

Electric field 610, thus, induces electrophoresis in the analyte fluid which provides mass/size separation of the constituents of the analyte fluid flowing through flow channel 210. In the absence of electrophoresis or the electric field 610 and the gel material, the inertial and the fluid dynamic forces cause the larger particles to flow as per their initial relative positions at a lower velocity. The smaller particles, on the other hand, tend to congregate along the walls of flow channel 210. In electrophoresis, smaller molecules tend to move more easily through the gel and aggregate towards the bottom of the flow channel more quickly than larger molecules which tend to take a longer period of time to migrate to the bottom of the channel. By selectively driving the constituents towards the bottom of flow channel 210 using electrophoresis, resonance wavelengths of constituents of various sizes/masses may be identified. The target molecules move down the flow channel according to sizes/masses, with smaller molecules passing through the whispering gallery resonator section 315 first, followed by larger molecules, thus creating a temporal distribution with respect to the molecular sizes of one or more constituents of the analyte fluid.

Figure 7:
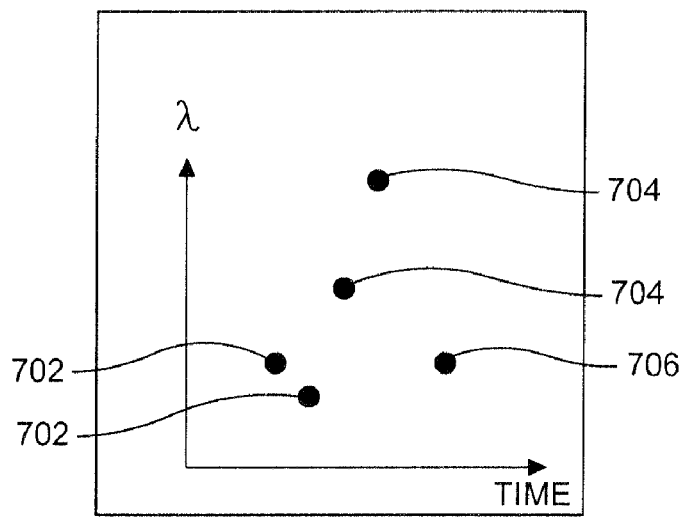
FIG. 7 is an exemplary time-spectral plot obtained from the system of FIG. 6.

Referring now to FIG. 7, a time-spectral plot 700 as generated from the output of system 600 is illustrated. Particles 702 represent relatively smaller particles, particles 704 represent relatively mid-size particles and particle 706 represents a relatively larger particle. Relatively smaller particles 702 are detected relatively earlier. Relatively larger particles 706, on the other hand, are detected relatively later.

Figure 8:
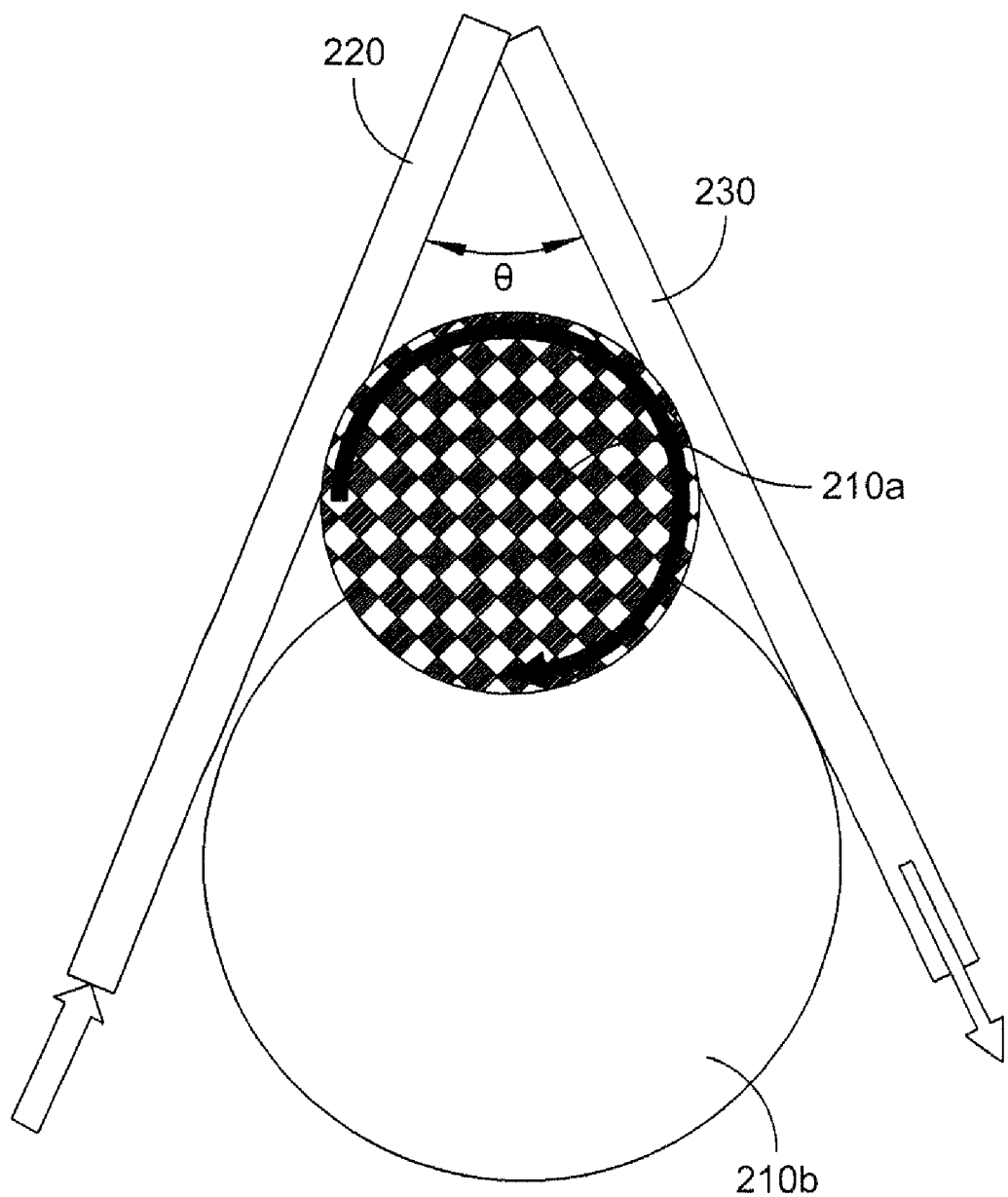
FIG. 8 illustrates an exemplary configuration of two optical waveguides for use in a system for direct optical interrogation of a fluid flowing through a flow channel, according to an embodiment of the invention.

Referring now to FIG. 8, an exemplary embodiment of first and second optical waveguides 220, 230 is illustrated. This embodiment is used without electrophoresis. First and second optical waveguides 220, 230 may be arranged permanently in a generally "V-shaped" configuration. In an exemplary embodiment, the V-shaped configuration may have an angle θ of about 45°. Any other angle θ greater than 0° and less than 180° may also be used depending on requirements of an application. Optical waveguides 220, 230 in such a V-shaped configuration can accommodate flow channels of different diameters within a given range depending on the length of optical waveguides 220, 230 and the angle therebetween. In the illustrated embodiment, a flow channel 210a with a smaller diameter as well as a flow channel 210b with a larger diameter may be accommodated between optical waveguides 220, 230 without having to adjust the positions of optical waveguides 220, 230 while still maintaining an evanescent field coupling between flow channel 210a or 210b and optical waveguides 220, 230. In another configuration, the angle between first and second optical waveguides 220, 230 may be adjustable to provide further flexibility in terms of the range of diameters of flow channels which can be accommodated therebetween.

Figure 9D:
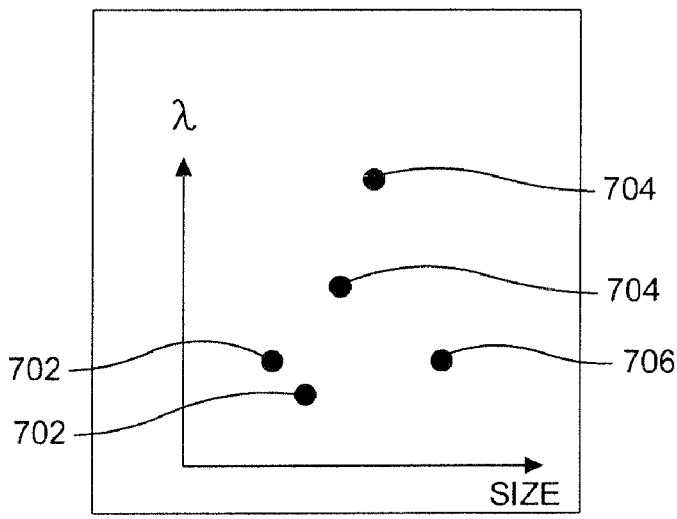
FIG. 9D is an exemplary size-spectral plot obtained from the system of FIG. 9A, based on pure dynamic fluid flow with multiple tube diameter transitions.
Figures 9A, 9B, 9C:
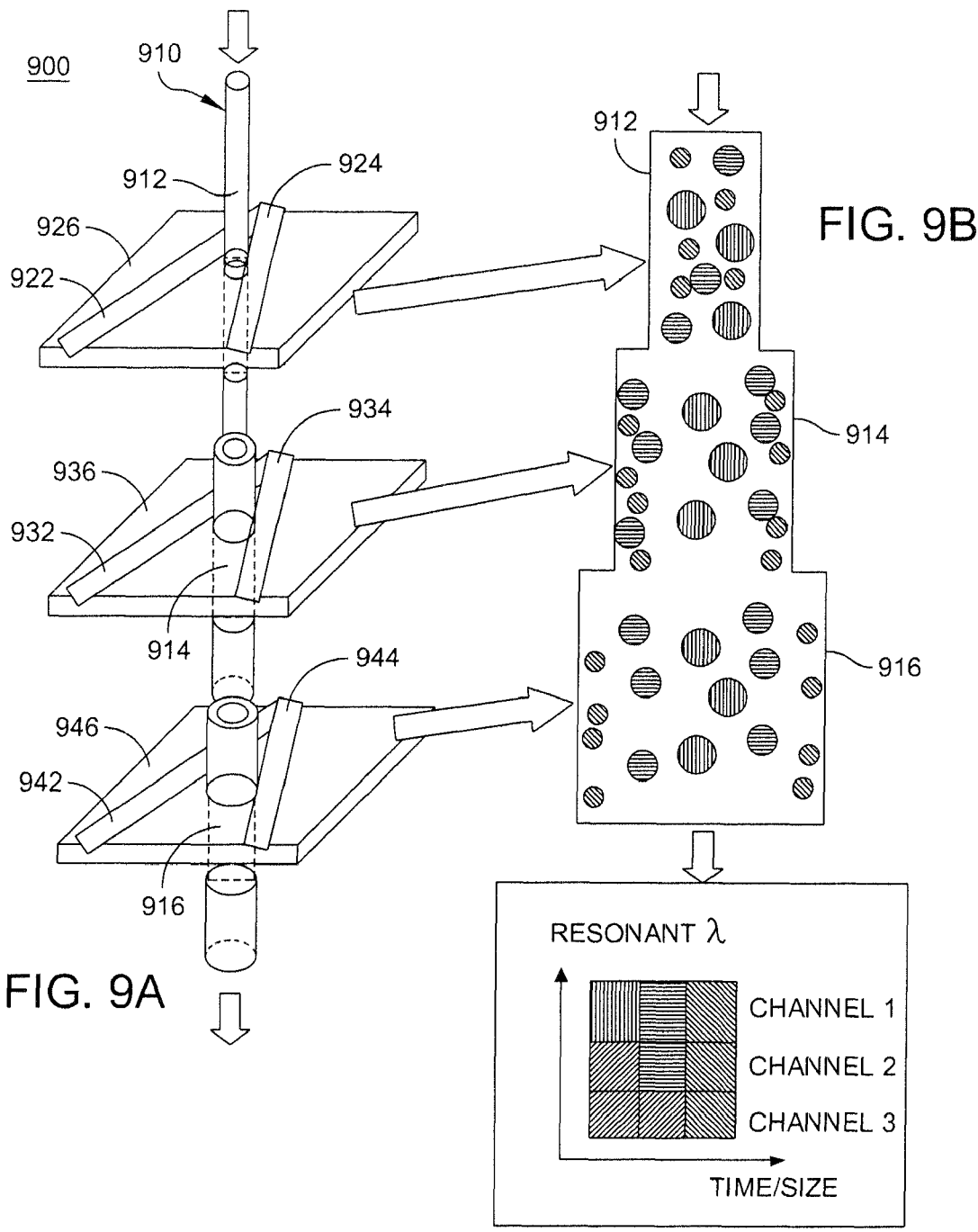
FIG. 9A is a schematic diagram of a system for direct optical interrogation of a fluid flowing through a flow channel having varying cross-sections, according to yet another embodiment of the invention.
FIG. 9B is a cross-sectional view of the flow channel of FIG. 9A with an analyte fluid flowing therethrough.
FIG. 9C is an exemplary plot of resonance wavelengths for constituents of different masses.

Referring to FIGS. 9A-9B, another exemplary embodiment 900 for optical interrogation of an analyte fluid is illustrated. In one configuration, flow channel 910 includes three sections 912, 914, 916 each having a diameter different than the other. Each section 912, 914, 916 has a corresponding set of first and second optical waveguides positioned on corresponding platform. For example, first and second optical waveguides 922, 924 on a platform 926 are optically coupled with section 912; first and second optical waveguides 932, 934 on a platform 936 are optically coupled with section 914; and first and second optical waveguides 942, 944 on a platform 946 are optically coupled with section 916. In the illustrated embodiment, the diameters of sections 912, 914, 916 progressively increase in the direction of the flow of the analyte fluid through flow channel 910. In another embodiment, the diameters of sections 912, 914, 916 progressively decrease in the direction of the flow of the analyte fluid through flow channel 910. For such a configuration with the decreasing diameters in the direction of the analyte fluid flow, one skilled in the art will understand that the smaller diameter sections serve as a filter for the spatially size-distributed particles. Such particles not passing through the filter thus need to be removed in order not to clot up the channel. On the other hand, flow structure with diameters increasing in the direction of the flow does not change the constituents of the flow materials.

As the analyte fluid flows through flow channel 910, the heavier/bigger constituents of the analyte fluid tend to aggregate towards the center of flow channel 910 and the lighter/smaller constituents of the analyte fluid tend to aggregate towards the walls of flow channel 910 and this is in contrast to the flow-spin approach described herein above. Optical interrogation of the analyte fluid at each of sections 912, 914, 916 provides unique identifying wavelength signature of differently sized analyte fluid constituents. As is known in the art, in a whispering gallery mode resonator, optical energy circulates internally about the surface of the resonator. Since section 912 is relatively smaller, constituents of varying sizes may be generally randomly distributed along the wall of flow channel 910. The shift in resonance wavelength, as detected by optical waveguide 924, is, therefore, generally indicative of constituents of all sizes, as indicated by "Channel 1" on FIG. 9C. Section 914 is relatively larger compared to section 912. Therefore, constituents of the largest sizes tend to aggregate away from the wall of flow channel 910. The shift in resonance wavelength, as detected by optical waveguide 934, is, therefore, generally indicative of the constituents of generally smaller sizes, as indicated by "Channel 2" on FIG. 9C. As Section 916 is the largest among the three illustrated sections. Therefore, only the constituent of generally the smallest sizes tend to aggregate about the wall of flow channel 910. The shift in resonance wavelength, as detected by optical waveguide 944, is indicative of the constituents of generally the smallest sizes, as indicated by "Channel 3" on FIG. 9C. Thus, a single flow-channel 910 with different diameters may be used to identify different constituents of different sizes in the analyte fluid flowing through flow channel 910, using multiple sets of first and second optical waveguides.

Referring now to FIG. 9D, a size-spectral plot, analogous to that illustrated in FIG. 7 may be obtained using the embodiment of FIG. 9A. Relatively smaller particles 702 have a relatively smaller shift in the resonance wavelength. Relatively larger particles 704, 706, on the other hand, have a relatively larger shift in the resonance wavelength. Thus, a flow channel 910 with increasing cross-sections may achieve similar size/mass differentiation of the analyte fluid particles as that obtained by the inducement of electrophoresis in continuous fluid flow condition.

Figure 12:
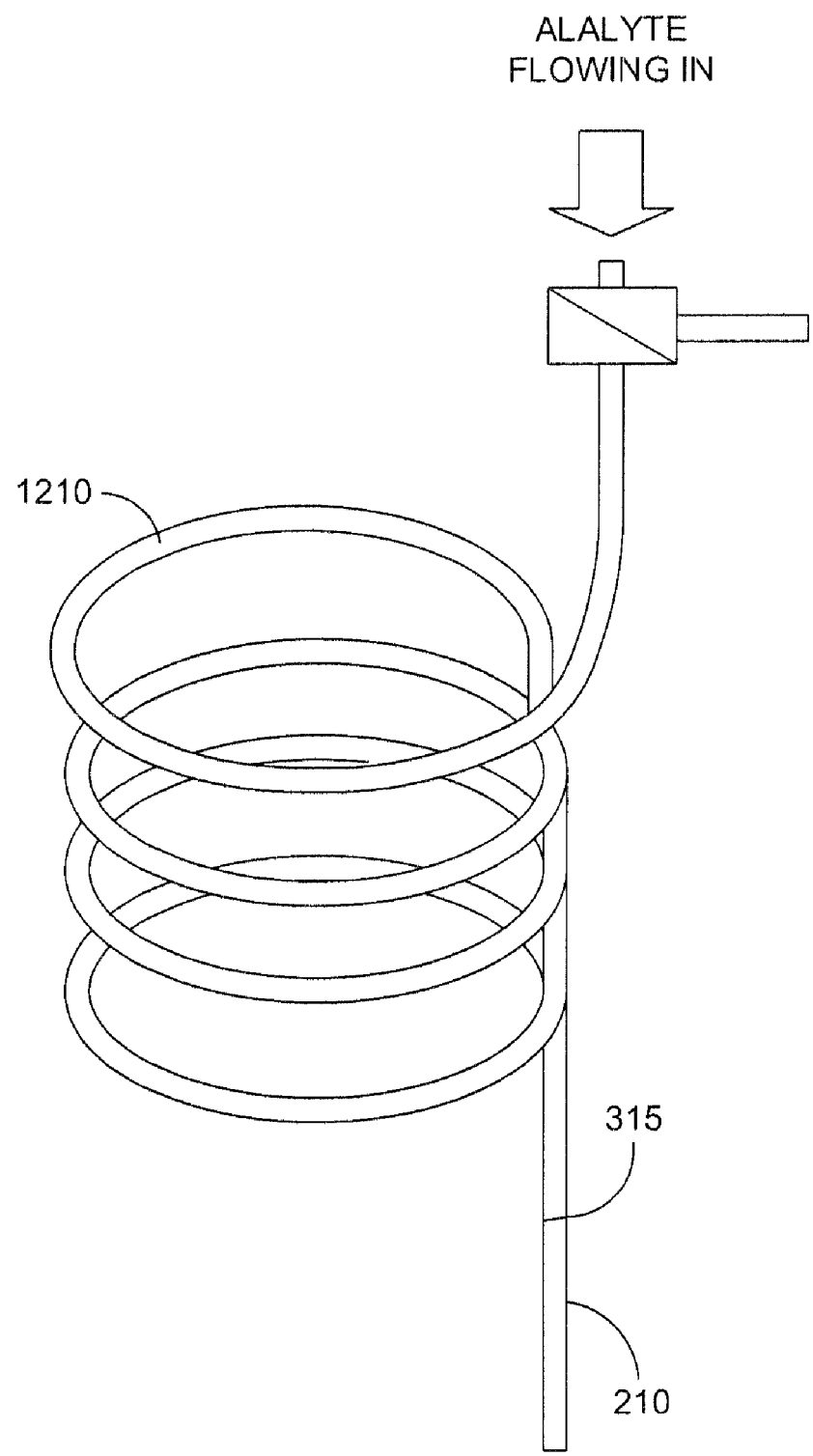
FIG. 12 is a schematic view of a spin imparting mechanism for a flow channel of FIG. 1, according to an embodiment of the invention.

Referring now to FIG. 12, in yet another embodiment, a curved tube 1210 that imparts spin motion to the fluid flow may be used as a size separator or a filter and, therefore, as a preprocessor to separate out particles of different sizes and channel them into one or more flow channels 210 for identification using the optical whispering gallery mode technique. System 200 in this embodiment may include multiple flow channels 210 with associated first and second optical waveguides 220, 230. An advantage of the flow-spin approach is the larger or heavier particles may be positioned toward the wall of flow channel 210. Another advantage of using the flow-spin approach is various constituents of an analyte fluid may be segregated according to their mass and size and may be fed into different flow channels 210 for more accurate identification of multiple constituents in a single analyte fluid. One or more pre-processors, upstream of assembly 200, may sort particles of different sizes and may inject analyte fluids containing different sized particles into different flow channels 210 for optical interrogation using the whispering gallery mode resonance technique described herein.

An advantage of the system described herein is the label-free optical diagnostic of an analyte fluid. Another advantage of the system described above is that an analyte fluid flowing through a flow channel may be analyzed in real-time. A further advantage of the system using a first optical waveguide for transmitting an optical signal to the WGM section and a second optical waveguide for transmitting an output optical signal from the WGM section is that input transmission loss may be monitored via the first optical waveguide while only the light coupled to the WGM section is transmitted via the second optical waveguide, without the input light interfering with the output signal from the WGM section. Thus, the dual waveguide approach provides a larger dynamic signal-to-noise ratio, since the coupled detected output light does not have a large signature background to mask the detected signal. Yet another advantage of the flow channel having different diameter sections and multiple optical whispering gallery mode resonance probes is that analyte fluid constituents of different mass and sizes may be identified. Yet another advantage of the system described herein is that the system is a portable system which may be quickly and easily deployed for real-time diagnostics in the field.

While the foregoing invention has been described with reference to the above-described embodiment, various modifications and changes can be made without departing from the spirit of the invention.

What is claimed is:

1. A whispering gallery mode resonator based optical sensor assembly comprising:
   a flow channel permeable to optical energy,
   first and second optical waveguides adjacent to a first section of said flow channel and adapted to be in first and second evanescent field couplings respectively with said first section, such that said first section forms a first whispering gallery mode resonator responsive to a first optical signal conveyed in said first optical waveguide and communicates a second optical signal to said second optical waveguide indicative of a resonance wavelength of the whispering gallery mode resonator;
   a first detector optically coupled to the second optical waveguide for detecting the output signal; and
   a signal processor for detecting a shift in the output signal responsive to an analyte fluid flowing through said first section, said shift being indicative of the identity of at least one constituent of the analyte fluid;
   wherein said first and second optical waveguides are arranged in a generally "V-shaped" configuration, defining an angle therebetween, wherein said angle between said first and second optical waveguides is adjustable.

2. The optical sensor assembly of claim 1, wherein said first and second optical waveguides comprises at least one of single-mode optical fibers, multi-mode optical fibers, and tapered optical fibers.

3. The optical sensor assembly of claim 2, wherein first and second optical waveguides are substantially parallel to each other, separated by said section.

4. The optical sensor assembly of claim 1, further comprising an anode and a cathode for applying an electric field to said flow channel, thereby inducing electrophoresis in the analyte fluid flowing through said flow channel.

5. A whispering gallery mode resonator based optical sensor assembly comprising:
 a flow channel permeable to optical energy;
 first and second optical waveguides adjacent to a first section of said flow channel and adapted to be in first and second evanescent field couplings respectively with said first section, such that said first section forms a first whispering gallery mode resonator responsive to a first optical signal conveyed in said first optical waveguide and communicates a second optical signal to said second optical waveguide indicative of a resonance wavelength of the first whispering gallery mode resonator;
 a first detector optically coupled to the second optical waveguide for detecting the second output signal;
 at least a second section of said flow channel, wherein said first section has a first diameter and said second section has a second diameter, said second diameter being different than said first diameter;
 third and fourth optical waveguides adjacent to said second section and adapted to be in third and fourth evanescent field couplings respectively with said second section, such that said second section forms a second whispering gallery mode resonator responsive to a third optical signal conveyed in said third optical waveguide and communicates a fourth optical signal to said fourth optical waveguide indicative of a resonance wavelength of the second whispering gallery mode resonator;
 a second detector optically coupled to the fourth optical waveguide for detecting the fourth signal; and
 a signal processor coupled to said first and second detectors for detecting a shift in the first and fourth output signals responsive to an analyte fluid flowing through said first and second sections, said shift being indicative of the identity of at least one constituent of the analyte fluid.

6. The optical sensor assembly of claim 5, wherein the second section follows said first section in the direction of flow of the analyte fluid in said flow channel and wherein said first diameter is smaller than said second diameter.

7. The optical sensor assembly of claim 5, wherein the second section follows said first section in the direction of flow of the analyte fluid in said flow channel and wherein said first section diameter is larger than said second section diameter.

8. A whispering gallery mode based optical sensor system comprising:
 at least one flow channel permeable to optical energy,
 first and second optical waveguides adjacent to a first section of said at least one flow channel and adapted to be in first and second evanescent field couplings respectively with said first section;
 a light source in optical communication with said first optical waveguide,
 wherein said first section forms a first whispering gallery mode resonator responsive to a first optical signal conveyed in said first optical waveguide from said light source and communicates a second optical signal to said second optical waveguide indicative of a resonance wavelength of the whispering gallery mode resonator;
  an optical detector optically coupled to the second optical waveguide for detecting the second optical signal;
  a digital signal processor in communication with said optical detector for detecting a shift in the output signal responsive to an analyte fluid flowing through said first section, said shift being indicative of the identity of at least one constituent of the analyte fluid; and
 a curved tube coupled to the flow channel, the curved tube imparting spin motion to the analyte fluid for segregating the larger or heavier particles in the analyte fluid toward a wall of the flow channel.

9. The system of claim 8, wherein said light source comprises a wavelength tunable light source.

10. The system of claim 8, wherein said light source comprises at least one Light Emitting Diode (LED).

11. The system of claim 8, wherein said optical detector comprises at least one of a Charge-Coupled Device (CCD) array, an optical prism, and an optical axis grating.

12. The system of claim 8, further comprising a database of a plurality of constituents of the analyte fluid and shifts in resonance wavelengths associated therewith.

13. The system of claim 8, further comprising a size separator for separating particles of different sizes within the analyte fluid.

14. A method for optical interrogation of an analyte fluid, said method comprising the steps of:
 conveying a first optical signal via a first optical waveguide evanescent field coupled to a first section of a flow channel, said first section defining a first whispering gallery mode resonator, said flow channel evanescent field coupled to a second adjacent optical waveguide to introduce a whispering gallery mode resonance in said first section of the flow channel providing a second optical signal in said second optical waveguide;
 detecting said second optical signal to identify a reference resonance wavelength;
 conveying a third optical signal via a third optical waveguide evanescent field coupled to a second section of a flow channel, said second section defining a second whispering gallery mode resonator, said flow channel evanescent field coupled to a fourth adjacent optical waveguide to introduce a whispering gallery mode resonance in said second section of the flow channel providing a fourth optical signal in said fourth optical waveguide, said second section following said first section in the direction of flow of analyte fluid in said flow channel and wherein said first section has a different diameter than said section;
 detecting said fourth optical signal to identify a reference resonance wavelength;
 flowing an analyte fluid through the flow channel;
 detecting an optical signal output from said second waveguide to identify a shift in the resonance wavelength of output relative to the reference resonance wavelength and indicative of the identity of at least one constituent of the analyte fluid; and
 detecting an optical signal output from said fourth waveguide to identify a shift in the resonance wavelength of output relative to the reference resonance wavelength and indicative of the identity of at least one constituent of the analyte fluid.

15. The method of claim 14, further comprising the step of generating the first optical signal using a wavelength tunable light source for conveying the optical signal to said first optical waveguide.

16. The method of claim 14, further comprising the step of applying an electric field to flow channel for inducing electrophoresis in the analyte fluid flowing through the flow channel.

17. The method of claim 14, wherein the second section follows said first section in the direction of flow of the analyte fluid in said flow channel and wherein said first section diameter is smaller than said second section diameter.

18. A method for optical interrogation of an analyte fluid, said method comprising the steps of:

conveying a first optical signal via a first optical waveguide evanescent field coupled to a section of a flow channel, said section defining a whispering gallery mode resonator, said flow channel evanescent field coupled to a second adjacent optical waveguide to introduce a whispering gallery mode resonance in said section of the flow channel providing a second optical signal in said second optical waveguide;

detecting said second optical signal to identify a reference resonance wavelength;

flowing an analyte fluid through the flow channel; and detecting an optical signal output from said second waveguide to identify a shift in the resonance wavelength of output relative to the reference resonance wavelength and indicative of the identity of at least one constituent of the analyte fluid.

wherein the step of flowing an analyte fluid further comprises the step of imparting spin motion to the analyte fluid for segregating the larger or heavier particles in the analyte fluid toward a wall of the flow channel.

* * * * *